United States Patent [19]

Dawson

[11] Patent Number: 5,407,920
[45] Date of Patent: Apr. 18, 1995

[54] TREATMENT OF WOOD AND TIMBER WITH PESTICIDAL FORMULATIONS

[75] Inventor: Howard B. Dawson, Derby, England

[73] Assignee: NC Development, Inc., Irving, Tex.

[21] Appl. No.: 111,907

[22] Filed: Aug. 26, 1993

Related U.S. Application Data

[60] Division of Ser. No. 668,500, Mar. 29, 1991, Pat. No. 5,242,907, which is a continuation-in-part of Ser. No. 435,441, Nov. 20, 1989, Pat. No. 5,037,653.

[30] Foreign Application Priority Data

Sep. 30, 1988 [GB] United Kingdom ............ 8822936

[51] Int. Cl.$^6$ ............ A01N 25/00; A01N 37/34; A01N 65/00; A01N 31/275
[52] U.S. Cl. .................. 514/65; 514/66; 514/68; 514/73; 514/521; 514/531; 514/937; 514/938; 514/939; 514/941; 424/405
[58] Field of Search ............ 514/531, 521, 89, 65, 514/66, 68, 73, 937, 938, 939, 941; 424/405

[56] References Cited

U.S. PATENT DOCUMENTS

| | | | |
|---|---|---|---|
| 3,954,967 | 5/1976 | Urton | 424/81 |
| 4,567,161 | 1/1986 | Posanski et al. | 514/23 |
| 5,037,653 | 8/1991 | Dawson | 514/521 |

FOREIGN PATENT DOCUMENTS

| | | |
|---|---|---|
| 1007985 | 4/1977 | Canada . |
| 1209361 | 8/1986 | Canada . |
| 062181 | 10/1982 | European Pat. Off. . |
| 092457 | 10/1983 | European Pat. Off. . |
| 107009 | 5/1984 | European Pat. Off. . |
| 149051 | 7/1985 | European Pat. Off. . |
| 302701 | 2/1989 | European Pat. Off. . |
| 0302701 | 8/1989 | European Pat. Off. . |
| 1026169 | 4/1953 | France . |
| 2187226 | 1/1974 | France . |
| 88/07326 | 10/1988 | WIPO . |

OTHER PUBLICATIONS

Berry et al., "Emulsion-based Formulations for Remedial Treatments Against Woodworm", BRE Information, Oct. 1983.

Duve et al., "Hoechst Glycol Ethers (Butyl Glycol)", Hoechst Solvents—Manual for Laboratory and Industry, 5th Ed., 1975, pp. 160–165.

*Primary Examiner*—Nathan M. Nutter
*Attorney, Agent, or Firm*—Foley & Lardner

[57] ABSTRACT

A method of treating wood and timber is disclosed. Wood or timber is treated with a pesticidal microemulsion or other water-miscible formulation that has an average particle size of at most 200 nm. The treatment is particularly effective in protecting wood and timber against the common furniture beetle (Anobium punctatum), the house longhorn (Hylotrupes bajulus), the death watch beetle (Xestobium rufovillorum), dry rot (Serpula (merulius) lacrymans) and wet rot (Coniophora puteena).

19 Claims, No Drawings

TREATMENT OF WOOD AND TIMBER WITH PESTICIDAL FORMULATIONS

This application is a division, of application Ser. No. 07/668,500, filed Mar. 29, 1991, and now U.S. Pat. No. 5,242,904 (national state of PCT/GB89/01160, filed Sep. 29, 1991), which is a CIP of U.S. Ser. No. 07/435,441, filed Nov. 20, 1989 and now U.S. Pat. No. 5,037,653, PCT/GB88/00239, filed Mar. 30, 1988).

This invention relates to the protection of crops and the control of pests. Crops that can be protected by means of the invention include tropical and temperate crops and pests which can be controlled by the invention include insect and acarine pests which infest these crops, public health pests and pests which infest or affect wood or timber and other building materials.

More particularly, the invention relates to formulations of water-insoluble oil-soluble substances in water as small particles whose Z average mean size particle size is less than 200 nm. (The Z average mean size can be defined as the model free mean of light scattering.) Such formulations include microemulsions, micellar solutions and molecular solutions.

Microemulsions are one of three identified types of dispersion (as distinct from a molecular solution) of oil, water and surfactant. (The term "oil" is used in this specification to mean any non-aqueous solvent in which a substance of interest is soluble and which is immiscible with water.) These three types of dispersion are: microemulsions, micellar solutions and normal emulsions (or macroemulsions).

Macroemulsions appear white or opaque and are characterised by their property to separate into their two original liquid phases on standing; the average particle diameter will generally be above 200 nm. Microemulsions and micellar solutions are translucent and do not separate. Microemulsions can be considered as having average droplet (or particle) diameters of from 10 to 200 nm, micellar solutions as having average particle diameters of from 2 nm to 10 nm and molecular solutions as having average particle diameters of less than 2 nm. Recent evidence, however, does suggest that microemulsions with droplet diameters below 10 nm are possible. As with macroemulsions, microemulsions can be of the water-in-oil (w/o) or oil-in-water (o/w) type and can be made to invert from one to another.

One of the best means of differentiating between formulations useful in the invention and macroemulsions (and between microemulsions, micellar solutions and molecular solutions) is on the basis of particle or droplet size (usually measured as averages). Average particle or droplet size may be measured with a laser particle sizer, such as the MALVERN AUTOSIZER 2c (Malvern Instruments, Malvern, Hereford & Worcester) using glass cells as sample containers.

Other techniques can be used to determine additional or alternative characteristics of formulations of this invention. These include x-ray studies, electron microscopy, light scattering depolarisation and nmr. In general, nmr measurements are used to resolve theoretical questions regarding the state or location of molecules in microemulsions. The line width for protons in molecules can indicate freedom of the molecules to thermal motion, the broadening of the line indicating greater restriction of motion. The chemical shift of water is different when it is distributed in spheres or in cylindrical or lamellar micelles. Other studies are possible using nmr, in addition.

FR-A-2187226 corresponds to CA-A-1007985 and discloses insecticidal compositions comprising an anionic surfactant and a hydrotrope.

FR-A-1026169 discloses various emulsions, which may be useful in formulating insecticides comprising an alkylsulphonate surfactant and a polar compound such as an alcohol, an amino, a phenol or an acid.

U.S. Pat. No. 3,954,967 discloses "microcolloids" containing a resin and a polar solvent.

EP-A-0062181 relates to apparently conventional emulsions containing high HLB surfactants.

EP-A-0107009 corresponds to CA-A-1209361 and relates to a development of the subject matter disclosed in EP-A0062181; again, emulsions containing high HLB surfactants are disclosed.

EP-A-0149051 corresponds to U.S. Pat. No. 4,737,520 also discloses certain emulsion formulations.

U.S. Pat. No. 4,567,161 discloses liquid active ingredient concentrates for the preparation of microemulsions. The microemulsions are stated to be oil-in-water microemulsions. The coemulsifiers are a particular class of glycerin esters having HLB (Hydrophilic/Lipophilic Balance) values of between 12 and 18. The formulations of U.S. Pat. No. 4,567,161 are said to have special significance for pharmaceutical active substances. However, the active ingredient can be a number of other substances including herbicides (a number of which are listed), fungicides, insecticides, acaricides, nematocides or plant growth regulators. No specific fungicides, insecticides, acaricides, nematocides or plant growth regulators are disclosed or even suggested.

WO-A-8807326, published on 6th Oct. 1988 and incorporated herein by reference, relates specifically to the use of pesticidal water-miscible formulations whose average particle sizes are at most 200 nm in the protection of cabbages and apples and/or in the control of grey aphids on cabbages (Brevicoryne brassicae), caterpillars on cabbages (Pieris brassicae), Tortrix larvae in apples and blowfly larvae, and to the protection of stored grain against the lesser grain borer weevil (Rhysopertha dominica).

It has now been found that certain formulations of insecticide/acaricides such as pyrethroids (for example, deltamethrin, cypermethrin or permethrin) show good or enhanced biological activity in the protection against other temperate and tropical crops, particularly rice, maize, cotton, soya and fruit other than apples and/or in the control of pests detrimental to such crops, as well as activity against a range of public health pests including houseflies, cockroaches and mosquitoes and pests which infest or affect wood or timber and other building materials.

According to a first aspect of the present invention, there is provided a method of protecting tropical and temperate crops, other than cabbages and apples, comprising treating the crops, or a locus for the crops, with an insecticidal and/or acaricidal water-miscible formulation whose average particle size is at most 200 nm; the formulation may comprise water, an insecticidal and/or acaricidal oil, a surfactant and a cosurfactant, the cosurfactant preferably having an HLB of less than 12.

The crop to be protected may be, for example, rice, maize, cotton, soya and fruit other than apples.

According to a second aspect of the present invention, there is provided a method of controlling insect pests of the order Lepidoptera (other than Totrix larvae and *Pieris brassicae*), Diptera, Coleoptera, Hemiptera (other than *Brevicoryne brassicae*), Orthoptera, Dictyoptera, Hymenoptera or Isoptera and/or acarine pests, the method comprising treating the pests, or a locus for the pests, with an insecticidal and/or acaricidal water-miscible formulation whose average particle size is at most 200 nm; the formulation may comprise water, an insecticidal and/or acaricidal oil, a surfactant and a cosurfactant, the cosurfactant preferably having an HLB of less than 12.

Members of the order of Lepidoptera which can be controlled include the small cabbage white (*Pieris rapae*) butterfly, the diamond-back moth (*Plutella xylostella*), the codling moth (*Cydia pomonella*), cutworms (*Agrotis spp*), the flour moth (*Anagasta kuhniella*), *Trichoplusia ni, Earias insulana,* army worms (*Spodoptera littoralis* and *S. exigua*), corn leaf worm (*Heliothis armigera* and *H. virescens*), *Chilo suppresalis* and *Bombyx mori.*

Members of the order Diptera which can be controlled include carrot fly (*Psila rosae*), cabbage root fly (*Erioischia brassicae*), the chyrsanthemum leaf miner (*Chromatomyia syngensiae*), the house fly (Musca domestica), topical fruit flies including the Mediterranean fruit fly (*Ceratitis capitata*), the Oriental fruit fly (*Dacus dorsalis*) and melon fly (*Dacus curcubitae*) and the vector mosquitoes *Anopheles arabiensis, A. gambiae* and *Aedes aegypti.*

Members of the order Coleoptera which can be controlled include the mustard beetle (*Phaedon cochleariae*), the flour beetle (*Tribolium spp*) the back vine weevil, the common furniture beetle (*Anobium punctatum*), the house longhorn (*Hyloptrupes bajulus*) and the death watch beetle (*Xestobium rufovillosum*).

Members of the order Hemiptera which can be controlled include apids including the peach-potato aphid (*Myzus persicae*), the black bean aphid (*Aphis fabae*), the pea aphid (*Acrythosiphon psium*), the grain aphid (*Sitobion avenae*), the rose-grain aphid (*Metropholophium padi*), the bird-cherry-oat aphid (*Rhopalosiphum padi*), the glasshouse whitefly (*Trialeurodes vaporariorum*), the cotton whitefly (*Bemisia tabaci*), the rice leaf hopper (*Nephatettix virescens*), the rice brown plant hopper (*Nilaparvata lugens*) and the green shield bug (*Nezara viridula*).

Members of the order of Orthoptera which can be controlled include the house cricket (*Achaeta domestica*) and locusts (*Schistocerca gregaria* and *Locusta migratoria*).

Members of the order Dictyoptera which can be controlled include cockroaches in the genera Blatta and Periplaneta.

Members of the order of Hymenoptera which can be controlled include leaf cutting and other ants, including *Atta sextans, Acryomyrmex octospinosus, Megaphonera foetens, Monomorium pharaoenis, Ecophylla longinoda, Chromatogaster sp, Myrmicaria eumenoides,* and *Camponotus sp.*

Members of the order Isoptera which can be controlled include *Cryptotermes cyanocephalus, Postelectrotermes militaris, Coptotermes arvignathus, Schedorhinotermes malacconsis* and *Macrotermes bellicosus.*

According to a third aspect of the invention, there is provided a method of controlling public health pests, particularly the house fly (*Musca domestica*), cockroaches (*Blatta spp.* and *Periphlaneta spp.*) and mosquito (*Aedes aegypti*), the method comprising treating the pests, or a locus for the pests, with an insecticidal and/or acaricidal water-miscible formulation whose average particle size is at most 200 nm; the formulation may comprise water, an insecticidal and/or acaricidal oil, a surfactant and a cosurfactant, the cosurfactant preferably having an HLB of less than 12.

Partly because of the ability of formulations in accordance with the invention to be particularly good insecticidal formulations, the invention lends itself to the treatment of wood or timber articles, for example to guard against the common furniture beetle, the house longhorn and the death watch beetle as discussed above. Formulations of the invention are thus very suitable for treating roof and other structural timbers of buildings. This overcomes or mitigates the hitherto apparently insoluble problem of how to apply pesticide while avoiding high levels of solvent in confined parts of buildings such as roof spaces; not only are conventional formulations with their typically high solvent levels a considerable fire hazard on storage, mixing and spraying, especially in the presence of electrical wiring, but also they pose a health hazard for the operator.

According to a fourth aspect of the invention, there is provided a method of treating wood or timber, the method comprising applying to the wood or timber a pesticidal water-miscible formulation whose average particle size is at most 200 nm; the formulation may comprise water, a pesticidal oil, a surfactant and a co-surfactant, the co-surfactant preferably having an HLB of less than 12.

Formulations in accordance with the invention may as indicated above, be used to treat wood or timber articles or other building materials against insect and acarine pests, and additionally they may be used to treat them against fungus, mould, lichen, algae and other plant pests. Fungi which may be controlled by the invention include dry rot (*Serpula* (*merulius*) *lacrymans*) and wet rot (*Coniophora puteana*). Moulds which may be controlled by the invention include *Aspergillus spp., Penicillium spp., Paecilomyces spp.,*

*Alternaria spp.* and *Cladosporium spp.*

As indicated above, if the formulation is a microemulsion, the microemulsion will generally be clear or translucent, except in the viscoelastic gel phase. Micellar solutions and molecular solutions may additionally be clear.

The water can be tap water, although distilled water can be used. The amount of water in the microemulsion will depend on many factors but typically for w/o microemulsions will be from 20 to 70% w/v and for o/w microemulsions it shall be from 40 to 95% w/v. Some hardness in the water, although not essential, may in practice be beneficial. Between 100 and 200. ppm hardness (as $CaCO_3$) may be appropriate, particularly around 150 ppm or 160 ppm.

As previously stated, the oil need not merely be an "oil" in the sense of a petroleum fraction, although such oils are included; the term "oil" is used to mean any non-aqueous solvent in which a substance of interest is soluble and which is immiscible with water; alternatively, the substance of interest may itself be the oil. Having said that, the oil may be animal, vegetable, mineral or silicone or some other organic solvent which is water-immiscible, such as an optionally halogenated hydrocarbon. The hydrocarbon may be aliphatic or aromatic or have both aliphatic and aromatic moieties. Typical solvents include xylene, naphthalene, kerosene, isoparaffins and halogenated hydrocarbons.

The surfactant may be any typical emulsifier as found in most macroemulsion systems. The surfactant may be anionic, cationic, zwitterionic or nonionic. Anionic surfactants are more frequently used. Suitable anionic surfactants include hydrocarbon sulphates, sulphonates and sulphamates, especially compounds wherein the hydrocarbon moiety is an alkyl or alkylaryl group. Soaps (hydrocarbyl carboxylates) can also be used, as can sulphocarboxylic acids such as sulphosuccinic acid. Examples of specific anionic detergents that can be used include alkyl benzene sulphonates and sulphonic acids such as $C_8$ to $C_{16}$ alkyl benzene sulphonates and sulphonic acids including dodecyl benzene sulphonic acid (a predominately straight chain mixture of which compounds is sold under the trade mark NANSA SSA). The use of anionic surfactants which are acids, as opposed to salts, may be advantageous.

The selection of an appropriate surfactant can be made by one of skill in the art without undue experimentation. As a guiding principle, it should be borne in mind that it is highly preferable to match, in a chemical sense, the structure of the surfactant with the structure of the oil. For example, if the oil is aromatic, such as xylene or naphthalene, it is preferred to use a surfactant having an aromatic moiety, for example an alkyl benzene sulphonate or an alkyl naphthalene sulphonate. If the oil is aliphatic, an aliphatic surfactant is preferred such as an alkyl sulphonate or a dialkyl sulphosuccinate (such as dioctyl sulphosuccinate) or a soap. Another factor in determining the choice of surfactant is the type of microemulsion (w/o or o/w) to be produced. Low HLB surfactants (for example having an HLB of from 4 to 9, particularly 4 to 7) tend to stabilise w/o microemulsions and should therefore for preference be used for w/o microemulsions and high HLB surfactants (for example having an HLB of from 9 to 20, particularly 9 to 20) tend to stabilise o/w microemulsions and should thus be used for o/w microemulsions. HLB values may be measured by standard techniques.

After having made the initial selection (eg on the basis of HLB), further selection of the surfactant can be achieved be comparing one hydrophobic portion of the surfactant with the structure of the oil, as discussed above. Polar groups on the surfactant also play an important role and should be considered in the matching process.

An alternative or additional surfactant selection system is based on the phase inversion temperature (PIT) and can therefore be referred to as the PIT system. This system is based upon the temperature at which a surfactant causes an o/w emulsion to invert into a w/o emulsion. It provides information concerning the types of oils, phase volume relationships and the concentration of surfactant which could be used. This system is established on the proposition that the HLB of a nonionic surfactant changes with temperature; the inversion of an emulsion type occurs when the hydrophilic and lipophilic tendencies of the surfactant just balance. No emulsion forms at this temperature. Emulsions stabilised with nonionics tend to be o/w types at low temperatures and w/o types at high temperatures. From the microemulsion standpoint, the PIT system has a useful feature in that it can throw light on the chemical type of surfactant preferred to match a given oil.

Water-miscible formulations useful in accordance with the invention include a cosurfactant having an HLB of less than 12. Two classes of cosurfactants are normally preferred for use, although others may be used. Aliphatic alcohols (particularly primary aliphatic alcohols) are a first preferred class. They may have a carbon content of from 5 to 12 or more carbon atoms. Lower homologues (for example $C_5$ to $C_7$ alcohols) are used to stabilise certain formulations, including w/o microemulsions and alcohols above $C_8$ (optionally including $C_8$) tend to be used to stabilise other formulations, including o/w microemulsions.

Nonionic surfactants form a more versatile group of co-surfactants. They can be balanced with the primary surfactant to give systems that are stable as micellar solutions and as both w/o and o/w microemulsions. A whole range of nonionics can be used, including ethylene oxide propylene oxide block copolymers (as typified by the PLURONIC PE or PLURIOL PE range from BASF) and alcohol ethoxylates (as typified by the DOBANOL range from Shell).

The HLB of the cosurfactant may be less than 10 or even less than 5. For example, one nonionic cosurfactant is the ethylene oxide propylene oxide block copolymer containing 10% ethylene oxide sold under the trade mark PLURONIC PE 6100 or PLURIOL PE 6100, which has an HLB of 3.0. Other suitable HLB values for cosurfactants are less than 3, for example about 2 or even about 1. In other circumstances, a suitable cosurfactant HLB value of from 6 to 8, for example about 7, may be suitable; PLURONIC PE 6100 or PLURIOL PE 6100 is an example of a cosurfactant having such an HLB value.

Choosing an appropriate cosurfactant to be formulated with a surfactant and the other components of microemulsions in accordance with the inventions is possible to one of skill in the art without undue experimentation. The methods previously discussed in relation to the choice of surfactant can also be of assistance in the choice of cosurfactant. Further or in the alternative, the technique of cosurfactant partitioning can be of assistance in the preparation of microemulsions. This approach rests on the premise that the condition responsible for the spontaneous formation and stability of microemulsions came about with a zero (or transiently negative) interfacial tension. The total interfacial tension was given by the formula:

$$\gamma_i = (o/w) - \pi$$

Where
$\pi_i$ = total interfacial tension
$\gamma_{(o/w)}$ = interfacial tension before addition of stabilising agents and
$\pi$ = two dimensional spreading pressure in the monolayer of adsorbed species.

It was then proposed that the initial zero or negative value of the total interfacial tension was the result not so much of a high value of the two dimensional spreading pressure but of the large depression in the value of $(\gamma_{o/w})_a$, so that $\gamma_i = (\gamma_{(o/w)a}) - \pi$, where $(\gamma_{(o/w)a})$ is the interfacial tension after the addition of stabilising agents.

Since most microemulsions appear to form much more readily in the presence of a cosurfactant which is oil soluble, it has been assumed that this material distributed itself between the oil phase and the interface and subsequently changed the composition of the oil so that its interfacial tension was reduced to $(\gamma_{o/w})_a$. This provides a formula with a useful aid to help match emulsifiers (surfactants and cosurfactants) to oils for microemulsification. From an economic standpoint, it is of course desirable only to use a minimum of cosurfactant which is suitable for use in any formulation of the invention under consideration.

Using the cosurfactant partitioning technique, it has been discovered that for any given surfactant, a short chain cosurfactant will tend to produce a w/o system, whereas a long chain cosurfactant will tend to promote an o/w system. In the case of soaps, the larger the size of the (hydrated) cation, the more effective that particular soap will be in promoting an o/w microemulsion.

From the point of view of the present invention, it is immaterial whether the zero interfacial argument as a prerequisite for microemulsion stability is correct.

The argument has simply been given as an illustration of how the cosurfactant may be selected. It is accepted that the use of the film balance equation is an over-simplification. From the practical formulator's point of view, however, the expression $(\gamma_{o/w})_a$ can be valuable.

The relative proportions of the various ingredients of the formulations in accordance with the present invention can vary widely. For w/o microemulsions, micellar solutions and molecular solutions, broad and preferred ranges of the ingredients may be as follows:

| Ingredient | Broad w/v | Preferred w/v |
| --- | --- | --- |
| Oil (including dissolved substance if any) | 20 to 50% | 30 to 40% |
| Surfactant | 1 to 20% | 1 to 5% |
| Cosurfactant | 1 to 20% | 1 to 5% |
| Water | 20 to 70% | 50 to 70% |

In general the amounts of surfactant and cosurfactant should be kept as low as possible and the amount of water should be kept as high as possible. The above is subject always to the proviso that the total number of percentage parts of the ingredients cannot exceed 100.

For o/w microemulsions, the broad and preferred concentration ranges of the ingredients can be as follows:

| Ingredient | Broad w/v | Preferred w/v |
| --- | --- | --- |
| Oil (including dissolved substance if any) | 1 to 20% | 1 to 10% |
| Surfactant | 1 to 10% | 1 to 5% |
| Cosurfactant | 1 to 10% | 1 to 5% |
| Water | 40 to 95% | 70 to 90% |

Again, the above is subject always to the proviso that the total number of percentage parts of the ingredients cannot exceed 100.

A water-insoluble oil-soluble insecticide and/or acaricide which it is desired to formulate may be dissolved in an oil, although it is clear that the oil may itself be the active substance.

Synthetic pyrethroids are particular candidates for formulation by means of the present invention. One synthetic pyrethroid is deltamethrin, which is the common name for 3-(2,2-dibromoethenyl)-2,2-dimethyl-cyclopropane carboxylic acid cyano(3-phenoxyphenyl)-methyl ester. Deltamethrin is a potent synthetic pyrethroid insecticide/acaricide, the preparation of the racemic mixture of which is described in DE-A2439177. Deltamethrin is insoluble in water, but is soluble in organic solvents such as ethanol, acetone, dioxane, xylene and certain petroleum fractions.

Other synthetic pyrethroids include cypermethrin (3-(2,2-dichloroethenyl)-2,2-dimethylcyclopropane-carboxylic acid cyano(3-phenoxyphenyl)-methyl ester), permethrin (3-(2,2-dichloroethenyl)-2,2-dimethyl-cyclo-propanecarboxylic acid (3-phenoxyphenyl)-methyl ester) and fenvalerate (4-chloro-alpha-(1-methylethyl)benzene-acetic acid cyano (3-phenoxyphenyl) methyl ester. Cypermethrin may be prepared as described in DE-A2326077, permethrin may be prepared as described in DE-A-2437882 and DE-A-2544150, and fenvalerate may be prepared as described in DE-A-2335347. Apart from the synthetic pyrethroids, natural pyrethroids, organophosphorus compounds and carbamates are other examples of insecticide/acaricides useful in the present invention.

Organophosphorus compounds include chlorpyritos (O,O-diethyl-O-3,5,6-trichloro-2-pyridyl phosphorothioate), chlorpyrifos-methyl (O,O-dimethyl-O-3,5,6-tri-chloro-2-pyridyl phosphorothioate), fenitrothion (O,O-dimethyl-O-4-nitro-m-tolyl phosphorothioate) and pirimiphos-methyl (O-2-diethylamino-6-methylpyrimidin-4-yl-O,O-dimethyl phosphorothioate).

Mixtures of insecticide/acaricides (for example mixtures of pyrethroids or mixtures of pyrethroid(s) and organophosphorus compound(s)) may be particularly suitable for some applications. Cypermethrin is an example of a liquid which can function both as the oil and as a water-insoluble oil-soluble substance. When the oil is an insecticide/acaricide the formulation may be free of an oily solvent for the pesticide.

Other pesticides which can be formulated by means of the invention include fungicides and herbicides. Fungicides particularly useful for treating wood or timber or other building materials include pentachlorophenol, zinc salts including zinc octoate and zinc naphthenate, propaconazole and, particularly for dry rot, an alkali metal phenyl phenoxide, such as sodium 2-phenyl-phenoxide tetrahydrate.

With water-in-oil microemulsions, micellar solutions and molecular solutions, it is generally possible to get a higher concentration of the active substance (for example deltamethrin or another synthetic pyrethroid or other pesticide). However, o/w formulations may give a perfectly adequate concentration for end use or even for concentrates for dilution before use.

In principle, formulations in accordance with the invention can be made very simply. Therefore, formulations useful in the invention may be prepared by mixing the ingredients. Depending on the thermodynamic favourability of the system, the ingredients will tend to form a microemulsion, micellar solution or molecular solution. In practice, however, kinetic considerations may dictate that some agitation is preferably used to assist the mixing. Agitation may be by magnetic or mechanical means or in some cases ultrasonic.

Once a desired and correctly balanced formulation has been arrived at, it will be found that the order of addition of the ingredients is not normally critical. However, for w/o microemulsions, micellar solutions and molecular solutions, it is preferred to add the ingredients to a vessel in the following order:

1. Add the oil to a vessel
2. Add any additives such as solid deltamethrin dissolved in further oil
3. Add the surfactant and cosurfactant and dissolve them in the oil
4. Add water to give a clear formulation (eg a w/o microemulsion)

Although the above procedure may be found to be suitable for o/w microemulsions, there is a possibility that upon addition of the water, the system could move into the viscoelastic gel region (which can be almost solid) and this could cause practical mixing problems. Consequently, the following procedure is preferred for the preparation of o/w microemulsions:
1. The oil is added to the vessel
2. Additives (such as solid deltamethrin) is dissolved in the oil
3. The surfactant is added and dissolved in the oil
4. Water is added and agitated to give a homogeneous macroemulsion
5. The cosurfactant is added and the system is agitated to produce a clear o/w microemulsion. p Routine modifications, such as the application of heat or altering the degree of agitation can be made to these basic processes to suit the system in use.

Agricultural formulations useful in the invention may have a further advantage in that they use less potentially harmful solvent (such as xylene) per dose than certain conventional formulations, thereby posing less of a threat to the crop being treated, the handler and to the environment in general.

The concentration of the active substance (for example, deltamethrin) in the formulations useful in the invention may range from as little as 0.1 ppm, 0.01 g/l or 0.1 g/l up to 100 or 200 g/l or more. High concentrations of insecticide/acaricide may range from 10 to 300 g/l, for example 25 to 200 g/l, such as 25 or 100 g/l. For agricultural use of deltamethrin or another pyrethroid pesticide 10 to 50 g/l or 100 g/l final concentration may be found to be suitable. For public health or stored grain use, a formulation containing from 0.1 ppm or 0.05 g/1 to 5 g/1, for example 0.1 g/l to 1 g/l may be found to be acceptable.

The invention will be illustrated by the following preparations and examples.

Preparation 1

A w/o microemulsion was made up from the following ingredients:

| xylene/deltamethrin concentrate[1] | 200 ml/l |
|---|---|
| xylene | 200 ml/l |
| PLURIOL PE 6100[2] | 150 g/l |
| NANSA SSA[3] | 130 g/l |
| Water (tap) | 345 g/l |

Notes:
[1]The concentrate contained 125 g/l deltamethrin and gives a final concentration of 25 g/l
[2]Trade mark for ethylene oxide propylene oxide block copolymer containing 10% ethylene oxide, HLB 3.0-nonionic surfactant functioning as cosurfactant.
[3]Trade mark for dodecyl benzene sulphonic acid-predominantly straight chain (anionic surfactant).

A litre of the above formulation was prepared by first adding 200 ml xylene to a beaker. 200 ml of the xylene/deltamethrin concentrate was then added to the same beaker. The surfactant and cosurfactant were then added and dissolved in the oil phase. The water was then added, with stirring, to give a clear w/o microemulsion. The formulation was confirmed to be a microemulsion by conductivity measurements. The average particle size of a 1/400 dilution was measured by a MALVERN AUTOSIZER 2c laser particle sizer to be 62.8±11.8 nm.

Preparation 2

A formulation was prepared from the following ingredients:

| Deltamethrin | 0.4 g/l |
|---|---|
| Xylene | 25.75 g/l |

-continued

| NANSA SSA[2] | 36 g/l |
|---|---|
| Propylene oxide/ethylene oxide copolymer* | 41.2 g/l |
| Water | 906 g/l |

*Cosurfactant: Molar mass of polypropylene oxide portion = 1750 g/mol; percentage of polyethylene oxide in total molecule = 10%.

A litre of the above formulation was prepared by first adding the xylene to a beaker. Solid deltamethrin was then added and dissolved in the xylene. The NANSA SSA surfactant was then added and dissolved in the oily phase. Subsequently, water was added and the mixture agitated to give a homogeneous macroemulsion. Finally, the (PLURIOL PE 6100) cosurfactant was added and the entire system agitated to produce a clear formulation. The average particle size was measured by a MALVERN AUTOSIZER 2c laser particle sizer to be 0.8 nm, which indicates that the formulation is a molecular solution.

Preparation 3

A formulation was prepared from the following ingredients:

| Xylene/cypermethrin[1] | 400 ml/l |
|---|---|
| PLURIOL PE 6100 | 150 g/l |
| NANSA SSA | 130 g/l |
| Water | 345 g/l |

Note:
[1]100 g cypermethrin (technical) made up to 400 ml with xylene.
[2]Trade mark for dodecyl benzene.sulphonic acid - predominantly straight chain (anionic surfactant).

20 g cypermethrin were made up to 80 ml with xylene, and the resulting mixture was placed in a 250 ml beaker. The PLURIOL PE 6100 surfactant and NANSA SSA cosurfactant were then slowly dissolved into this and the appropriate amount of water (69.0 mls) added slowly from a burette while stirring. The formulation was confirmed to be a micellar solution by conductivity measurements. The average particle size of a 1/400 dilution was measured by a MALVERN AUTOSIZER 2c laser particle sizer to be 40.2±6.9 nm, showing the diluted formulation to be a microemulsion.

Preparation 4

A ready-for-use formulation was made up from the following ingredients:

| K'OTHRINE 50[1] | 8.0 ml/l |
|---|---|
| Xylene | 2.0 ml/l |
| PLURONIC PE 10 100[2] | 9.0 g/l |
| NANSA SSA | 6.0 g/l |
| Water | 976.0 g/l |

Notes:
[1]A 50 g/l solution of deltamethrin in xylene
[2]Trade mark for ethylene oxide propylene oxide block copolymer containing 10% ethylene oxide, HLB 3.0 - nonionic surfactant functioning as cosurfactant.

The K'OTHRINE and xylene were mixed and the surfactants dissolved into them; then the water was added from a burette with constant stirring. The average particle size was measured by a MALVERN AUTOSIZER 2c laser particle sizer to be 15.0±2.2 nm, showing the formulation to be on the lower size limit for a microemulsion.

Preparation 5

A ready-for-use formulation was made up from the following ingredients:

| | |
|---|---|
| K'OTHRINE 50[1] | 8.0 ml/l |
| Xylene | 2.0 ml/l |
| PLURONIC PE 10 100[2] | 12.0 g/l |
| NANSA SSA | 8.0 g/l |
| Water | 917.0 g/l |

Notes:
[1] A 50 g/l solution of deltamethrin in xylene
[2] Trade mark for ethylene oxide propylene oxide block copolymer containing 10% ethylene oxide, HLB 3.0 - nonionic surfactant functioning as cosurfactant.

The K'OTHRINE and xylene were placed in a beaker. To this the PLURIOL and NANSA were added; then this was well mixed. The water was added to this mixture with constant stirring. The average particle size was measured by a MALVERN AUTOSIZER 2c laser particle sizer to be 4.1±1.4 nm, showing the formulation to be a micellar solution.

Preparation 6

A formulation was made up from the following ingredients:

| | |
|---|---|
| K'OTHRINE 50[1] | 40.0 ml/l |
| NANSA SSA | 34.2 g/l |
| PLURONIC PE 6200[2] | 41.8 g/l |
| Filtered Tap Water | 889 g/l |

Notes:
[1] A 50 g/l solution of deltamethrin in xylene
[2] Trade mark for ethylene oxide propylene oxide block copolymer containing 20% ethylene oxide - nonionic surfactant functioning as cosurfactant.

40 ml K'OTHRINE, 34.2 g NANSA SSA and 41.8 g PLURIOL PE 6200 were placed in a beaker and then mixed with a stirrer. Then the 889 g water was added to this mixture with constant stirring. The average particle size was measured by a MALVERN AUTOSIZER 2c laser particle sizer to be 0.8 nm, showing the formulation to be a molecular solution. An 8% dilution had an average particle size of 73.0±14.3 nm, measured similarly, showing the diluted formulation to be a microemulsion.

Preparation 7

A formulation was made up from the following ingredients:

| | |
|---|---|
| Cypermethrin | 50 g/l |
| Xylene | 38.5 g/l |
| PLURIOL PE 8100[1] | 100 g/l |
| NANSA SSA | 53.8 g/l |
| Water | 757.7 g/l |

Note:
[1] Trade mark for ethylene oxide propylene oxide block copolymer containing 10% ethylene oxide (HLB = 2) - nonionic surfactant functioning as cosurfactant.

The cypermethrin was dissolved in the xylene; to this the PLURIOL PE 8100 and NANSA SSA were added and mixed in well. The water was added slowly with constant stirring until clear. The average particle size of a 400 dilution in water was measured by a MALVERN AUTOSIZER 2c laser particle sizer to be 41.2±7.0 nm, showing the formulation to be a microemulsion.

Preparation 8

A formulation was made up from the following ingredients:

| | |
|---|---|
| Cypermethrin | 50 g/l |
| PLURIOL PE 8100[1] | 130 g/l |
| NANSA SSA | 70 g/l |
| Water | 750 g/l |

Note:
[1] Trade mark for ethylene oxide propylene oxide block copolymer containing 10% ethylene oxide (HLB = 2) - nonionic surfactant functioning as cosurfactant.

The cypermethrin was dissolved in the PLURIOL PE 8100 and NANSA SSA. The water was added slowly with constant stirring until clear. The average particle size was measured by a MALVERN AUTOSIZER 2c laser particle sizer to be 7.8±1.6 nm, showing the formulation to be a micellar solution. It is expected that a microemulsion would be formed on dilution.

Preparation 9

A formulation was made up from the following ingredients:

| | |
|---|---|
| Cypermethrin | 95.6 g/l |
| Xylene | 36.8 g/l |
| PLURIOL PE 8100[1] | 124.3 g/l |
| NANSA SSA | 66.9 g/l |
| Water | 676.4 g/l |

Note:
[1] Trade mark for ethylene oxide propylene oxide block copolymer containing 10% ethylene oxide (HLB = 2) - nonionic surfactant functioning as cosurfactant.

The cypermethrin was dissolved in the xylene. To this the PLURIOL PE 8100 and NANSA SSA were added and mixed in well. The water was added slowly with constant stirring until clear. The average particle size was measured by a MALVERN AUTOSIZER 2c laser particle sizer to be 40.6±7.4 nm, showing the formulation to be a microemulsion.

Preparation 10

A formulation was made up from the following ingredients:

| | |
|---|---|
| Cypermethrin | 100 g/l |
| PLURIOL PE 8100[1] | 154 g/l |
| NANSA SSA | 83 g/l |
| Water | 663 g/l |

Note:
[1] Trade mark for ethylene oxide propylene oxide block copolymer containing 10% ethylene oxide (HLB = 2) - nonionic surfactant functioning as cosurfactant.

The cypermethrin was dissolved in the PLURIOL PE 8100 and NANSA SSA. The water was added slowly with constant stirring until clear. The average particle size was measured by a MALVERN AUTOSIZER 2c laser particle sizer to be 18.1±3.9 nm, showing the formulation to be a microemulsion.

Preparation 11

Following the general procedure of Preparation 1, a microemulsion of fenvalerate was prepared to a final concentration of 100 g/l.

Preparation 12

A formulation was made up from the following ingredients:

| | |
|---|---|
| Fenitrothion | 175 g/l |
| Deltamethrin | 25 g/l |
| Xylene | 180 g/l |
| PLURIOL PE 8100 | 150 g/l |
| NANSA SSA | 100 g/l |
| Water | 400 g/l |

The fenitrothion and the deltamethrin were dissolved in the xylene; to the resulting solution the PLURIOL PE 8100 and the NANSA SSA were added with stirring. Then the water was added slowly with constant stirring until clear. The average particle size of a 1/400 dilution in water was measured by a MALVERN AUTOSIZER 2c laser particle sizer to be 41.5±11.4 nm, showing the diluted formulation to be a microemulsion.

Preparation 13

A formulation was made up from the following ingredients:

|  |  |
|---|---|
| Chlorpyrifos-methyl | 175 g/l |
| Deltamethrin | 25 g/l |
| Xylene | 180 g/l |
| PLURIOL PE 8100 | 150 g/l |
| NANSA SSA | 100 g/l |
| Water | 400 g/l |

The chlorpyrifos-methyl and the deltamethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN AUTOSIZER 2c laser particle sizer to be about 40 nm, showing the diluted formulation to be a microemulsion.

Preparation 14

A formulation was made up from the following ingredients:

|  |  |
|---|---|
| Fenitrothion | 150 g/l |
| Cypermethrin | 50 g/l |
| Xylene | 180 g/l |
| PLURIOL PE 8100 | 150 g/l |
| NANSA SSA | 100 g/l |
| Water | 400 g/l |

The fenitrothion and the cypermethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN AUTOSIZER 2c laser particle sizer to be about 40 nm, showing the diluted formulation to be a microemulsion.

Preparation 15

A formulation was made up from the following ingredients:

|  |  |
|---|---|
| Chlorpyrifos-methyl | 150 g/l |
| Cypermethrin | 50 g/l |
| Xylene | 180 g/l |
| PLURIOL PE 8100 | 150 9/l |
| NANSA SSA | 100 g/l |
| Water | 400 g/l |

The chlorpyrifos-methyl and the cypermethrin were dissolved in the xylene; to the resulting solution the PLURIOL PE 8100 and the NANSA SSA were added with stirring. Then the water was added slowly with constant stirring until clear. The average particle size of a 1/400 dilution in water may be measured by a MALVERN AUTOSIZER 2c laser particle sizer to be about 40 nm, showing the diluted formulation to be a microemulsion.

EXAMPLE 1

Preparations useful in the invention were tested against the southern corn root worm (Diabrotica undecimpunctata at the 3rd-instar larvae stage. The application method was the standard Potter Tower method, and the application rate was 200 l/ha. Replicates of 10 larvae were placed in 10 cm Petri dishes on moist filter paper and sprayed. Maize seedlings were added and the larvae were kept at 20° C. with a 16h photoperiod. The following table shows the percentage of dead larvae at 24, 48 and 72h with all data corrected for control mortality. Preparations useful in the invention are compared with the standard AMBURSH cypermethrin emulsifiable concentrate and the standard DECIS deltamethrin emulsifiable concentrate.

| PRODUCT | PPM | No. TESTED | PERCENTAGE MORTALITIES | | |
|---|---|---|---|---|---|
|  |  |  | 24 h | 48 h | 72 h |
| AMBUSH | 100 | 30 | 0 | 39 | 89 |
|  | 50 | 30 | 4 | 18 | 75 |
|  | 25 | 30 | 3 | 3 | 7 |
|  | 12.5 | 30 | 0 | 0 | 10 |
| Preparation 3 | 100 | 30 | 0 | 25 | 89 |
|  | 50 | 30 | 0 | 25 | 68 |
|  | 25 | 30 | 7 | 13 | 17 |
|  | 12.5 | 30 | 0 | 0 | 3 |
| DECIS | 100 |  |  |  |  |
|  | 50 |  |  |  |  |
|  | 25 | 30 | 0 | 0 | 0 |
|  | 12.5 | 30 | 0 | 0 | 0 |
|  | 6.25 | 30 | 0 | 0 | 0 |
| Preparation 1 | 100 |  |  |  |  |
|  | 50 |  |  |  |  |
|  | 25 | 30 | 0 | 0 | 0 |
|  | 12.5 | 30 | 0 | 0 | 0 |
|  | 6.25 | 30 | 0 | 0 | 0 |

The percentage mortalities indicate that microemulsion formulations of cypermethrin and deltamethrin have good toxicity against the southern corn root worm.

EXAMPLE 2

Preparations useful in the invention were tested against Heliothis armigera at the 3rd-instar larvae stage. The application method Was a standard Potter Tower method, and the aplication rate was 200 l/ha. Replicates of 10 larvae were placed in 9 cm Petri dishes on moist filter paper and sprayed. Diet was added and the larvae were kept at 20° C. with a 16h photoperiod. The following table shows the percentage of dead larvae at 24, 48 and 72h, with all data corrected for control mortality, of preparations useful in the invention compared with the standard AMBUSH cypermethrin emulsifiable concentrate and the standard DECIS deltamethrin emulsifiable concentrate.

| PRODUCT | PPM | No. TESTED | PERCENTAGE MORTALITIES | | | |
|---|---|---|---|---|---|---|
|  |  |  | 24 h | 48 h | 72 h | 7 DAYS |
| AMBUSH | 100 | 10 | 0 | 0 | 30 | 100 |
|  | 50 | 30 | 0 | 14 | 22 | 22 |
|  | 25 | 30 | 8 | 11 | 8 | 8 |
| Preparation 3 | 100 | 10 | 0 | 10 | 0 | 100 |
|  | 50 | 30 | 7 |  |  |  |
|  | 25 |  |  |  |  |  |
| DECIS | 25 | 20 | 5 | 32 | 63 | 84 |
|  | 12.5 | 20 | 5 | 58 | 84 | 84 |
|  | 6.25 | 30 | 18 | 84 | 92 | 92 |
|  | 3.125 | 30 | 38 | 52 | 52 | 52 |
|  | 1.563 | 5 | 0 | 0 | 0 | 20 |
| Preparation 1 | 25 | 20 | 5 | 20 | 74 | 100 |
|  | 12.5 | 20 | 21 | 42 | 74 | 95 |

-continued

| PRODUCT | PPM | No. TESTED | PERCENTAGE MORTALITIES | | | |
|---|---|---|---|---|---|---|
| | | | 24 h | 48 h | 72 h | 7 DAYS |
| | 6.25 | 30 | 16 | 62 | 80 | 80 |
| | 3.125 | 10 | 5 | 65 | 88 | 88 |
| | 1.563 | 5 | 0 | 0 | 0 | 20 |

The deltamethrin microemulsion of Preparation 1 can be seen to be superior to DECIS at rates of 25 and 12.5 ppm.

EXAMPLE 3

Formulations useful in the invention were tested against Thrips tabaci at the late-instar nymph and adult stage. The application method was a standard Potter Tower method and the application rate was 200 l/ha. 5cm diameter discs were cut from marrow leaves and their abaxial surface was sprayed. The discs were then placed in Petri dishes on moist filter paper, treated surface uppermost. 10 Thrips were introduced to each dish, which was kept at 20° C. with a 16h photoperiod. The following table shows the percentage of dead Thrips at 24, 48 and 72h, with all data corrected for control mortality, for preparations useful in the invention, compared to a standard DECIS deltamethrin emulsifiable concentrate.

| PRODUCT | PPM | No. TESTED | PERCENTAGE MORTALITIES | | |
|---|---|---|---|---|---|
| | | | 24 h | 48 h | 72 h |
| Preparation 3 | 100 | 30 | 97 | 100 | 100 |
| | 50 | 30 | 100 | 100 | 100 |
| | 25 | | | | |
| | 12.5 | | | | |
| | 6.25 | | | | |
| | 3.125 | | | | |
| | 1.563 | | | | |
| DECIS | 25 | 10 | 90 | 100 | 100 |
| | 12.5 | 10 | 70 | 100 | 100 |
| | 6.25 | 20 | 90 | 100 | 100 |
| | 3.125 | 10 | 100 | 100 | 100 |
| | 1.563 | 30 | 53 | 66 | 66 |
| | 0.782 | 30 | 80 | 79 | 79 |
| | 0.391 | 30 | 37 | 35 | 41 |
| | 0.196 | 10 | 0 | 0 | 0 |
| Preparation 1 | 25 | 10 | 100 | 100 | 100 |
| | 12.5 | 10 | 80 | 90 | 90 |
| | 6.25 | 20 | 95 | 100 | 100 |
| | 3.125 | 10 | 100 | 100 | 100 |
| | 1.563 | 30 | 63 | 76 | 79 |
| | 0.782 | 30 | 57 | 62 | 66 |
| | 0.391 | 30 | 20 | 21 | 21 |
| | 0.196 | 10 | 20 | 18 | 18 |

The results show good activity of preparations useful in the invention against Thrips tabaci.

EXAMPLE 4

Compositions useful in the invention were tested against the army worm, Spodoptera litoralis at the 3rd-instar larvae stage. The application method was a standard Potter Tower method and the application rate was 200 l/ha. Replicates of 10 larvae were placed in 9 cm Petri dishes on moist filter paper and sprayed. Diet was added and the larvae were kept at 20° C. with a 16h photoperiod. The following table shows the percentage of dead larvae at 24, 48 and 72h and at 7 days for preparations useful in the invention compared to the standard AMBUSH cypermethrin emulsifiable concentrate and the standard DECIS deltamethrin emulsifiable concentrate. The percentage of dead larvae at 7 days was included since, for the higher doses, many larvae remained moribund at 72h. All data are corrected for control mortality.

| PRODUCT | PPM | No. TESTED | PERCENTAGE MORTALITIES | | | |
|---|---|---|---|---|---|---|
| | | | 24 h | 48 h | 72 h | 7 DAYS |
| AMBUSH | 25 | 30 | 0 | 60 | 87 | 100 |
| | 10 | 30 | 0 | 53 | 93 | 100 |
| | 5 | 30 | 10 | 30 | 50 | 73 |
| | 2.5 | 30 | 0 | 23 | 27 | 27 |
| | 1.25 | 30 | 0 | 10 | 10 | 27 |
| Preparation 3 | 25 | 30 | 0 | 40 | 80 | 100 |
| | 10 | 30 | 0 | 43 | 93 | 100 |
| | 5 | 30 | 20 | 27 | 40 | 83 |
| | 2.5 | 30 | 0 | 10 | 13 | 27 |
| | 1.25 | 30 | 0 | 0 | 0 | 0 |
| DECIS | 12.5 | 10 | 0 | 100 | 100 | 100 |
| | 5 | 10 | 20 | 100 | 100 | 100 |
| | 2.5 | 30 | 10 | 60 | 92 | 100 |
| | 1.25 | 30 | 7 | 47 | 44 | 72 |
| | 0.625 | 30 | 7 | 87 | 89 | 83 |
| | 0.313 | 30 | 3 | 13 | 3 | 5 |
| | 0.156 | 10 | 10 | 10 | 0 | 0 |
| Preparation 1 | 12.5 | 10 | 20 | 70 | 90 | 100 |
| | 5 | 10 | 30 | 100 | 100 | 100 |
| | 2.5 | 30 | 10 | 80 | 79 | 95 |
| | 1.25 | 30 | 3 | 63 | 71 | 83 |
| | 0.625 | 30 | 0 | 23 | 22 | 12 |
| | 0.313 | 30 | 3 | 10 | 12 | 0 |
| | 0.156 | 10 | 0 | 0 | 0 | 0 |

The results show good activity for the cypermethrin and deltamethrin microemulsion preparations useful in the invention.

EXAMPLE 5

Preparations useful in the invention were tested against Heliothis virescens at the 3rd-instar larvae stage. The application method was a standard Potter Tower method, and the application rate was 200 l/ha.

Replicates of 10 larvae were placed in 9 cm Petri dishes on moist filter paper and sprayed. Diet was added and the larvae were kept at 20° C. with a 16h photoperiod. The following table shows the percentage mortality of larvae at 24, 48 and 72h, with all data corrected for control mortality, for formulations useful in the invention, compared to the standard AMBUSH cypermethrin emulsifiable concentrate and the standard DECIS deltamethrin emulsifiable concentrate.

| PRODUCT | PPM | No. TESTED | PERCENTAGE MORTALITIES | | |
|---|---|---|---|---|---|
| | | | 24 h | 48 h | 72 h |
| AMBUSH | 100 | 30 | 87 | 100 | 100 |
| | 50 | 30 | 87 | 100 | 100 |
| | 25 | 30 | 70 | 76 | 86 |
| | 12.5 | 30 | 70 | 82 | 82 |
| | 6.25 | 30 | 28 | 69 | 74 |
| | 3.125 | 30 | 35 | 45 | 39 |
| | 1.563 | 30 | 10 | 14 | 5 |
| Preparation 3 | 100 | 30 | 100 | 100 | 100 |
| | 50 | 30 | 73 | 100 | 100 |
| | 25 | 30 | 33 | 93 | 97 |
| | 12.5 | 30 | 47 | 90 | 93 |
| | 6.25 | 30 | 56 | 87 | 89 |
| | 3.125 | 30 | 21 | 35 | 39 |
| | 1.563 | 30 | 28 | 28 | 26 |
| DECIS | 25 | 30 | 100 | 100 | 100 |
| | 12.5 | 30 | 87 | 100 | 100 |
| | 6.25 | 30 | 90 | 100 | 100 |
| | 3.125 | 30 | 83 | 97 | 100 |
| | 1.563 | 30 | 7 | 87 | 69 |
| | 0.782 | 30 | 31 | 52 | 69 |
| | 0.391 | 30 | 21 | 35 | 28 |
| Preparation 1 | 25 | 30 | 93 | 100 | 100 |
| | 12.5 | 30 | 100 | 100 | 100 |

-continued

| PRODUCT | PPM | No. TESTED | PERCENTAGE MORTALITIES | | |
|---|---|---|---|---|---|
| | | | 24 h | 48 h | 72 h |
| | 6.25 | 30 | 93 | 97 | 100 |
| | 3.125 | 30 | 83 | 97 | 100 |
| | 1.563 | 30 | 52 | 87 | 92 |
| | 0.782 | 30 | 35 | 52 | 46 |
| | 0.391 | 30 | 21 | 35 | 28 |

The results show that the formulation of Preparation 3 is more effective that then standard AMBUSH formulation at applied doses of 12.5, 6.25 and 1.563 ppm, where the final mortality is less than 100%. The deltamethrin microemulsion of Preparation 1 is superior to the DECIS preparation at an applied dose of 1.563 ppm.

EXAMPLE 6

Preparations useful in the invention were tested against the brown rice leaf hopper (Nilaparvata lugens) at the adult stage. The application method was a standard Potter Tower method and the application rate was 200 l/ha. Replicates of 10 nymphs were placed in 5cm Petri dishes, anaesthetised with a small jet of $CO_2$ and sprayed. The hoppers were then dropped onto a grou of potted rice plants (approximately 2 months old but cut down to a height of 15 cm). The plants were enclosed in a clear plastic collar with a lid of fine nylon mesh. The plants were kept at 20° C. with a 16h photoperiod. The following table shows the percentage of live hoppers at 24, 48 and 72h, with all data corrected for control mortality, for preparations useful in the present invention compared to the standard AMBUSH cypermethrin emulsifiable concentrate and the standard DECIS deltamethrin emulsifiable concentrate.

| PRODUCT | PPM | No. TESTED | PERCENTAGE MORTALITIES | | |
|---|---|---|---|---|---|
| | | | 24 h | 48 h | 72 h |
| AMBUSH | 400 | 30 | 66 | 97 | 100 |
| | 200 | | | | |
| | 100 | | | | |
| Preparation 3 | 400 | 30 | 93 | 100 | 100 |
| | 200 | | | | |
| | 100 | | | | |
| DECIS | 200 | 20 | 20 | 40 | 70 |
| | 100 | 28 | 18 | 29 | 57 |
| | 50 | 20 | 17 | 28 | 39 |
| | 25 | 32 | 22 | 28 | 34 |
| | 12.5 | 30 | 10 | 23 | 40 |
| | 6.25 | 29 | 3 | 3 | 20 |
| | 5 | 25 | 8 | 8 | 0 |
| Preparation 1 | 200 | 30 | 77 | 87 | 97 |
| | 100 | 30 | 40 | 57 | 77 |
| | 50 | — | — | — | — |
| | 25 | 32 | 30 | 43 | 50 |
| | 12.5 | 30 | 30 | 40 | 40 |
| | 6.25 | 29 | 17 | 20 | 20 |
| | 5 | 25 | 0 | 0 | 0 |

The activity of deltamethrin can be seen to be enhanced when sprayed as a microemulsion in accordance with the invention, compared to the DECIS formulation at applied rates of 12.5 ppm and above.

EXAMPLE 7

Preparations useful in the invention were tested against pyrethroid resistant first instar glasshouse whitefly (Trialeirodes vaporariorum) on french bean leaves. The replicate infested leaves were dipped in appropriate concentrations of the formulation under test and mortality was assessed after one week. A log dose probit response regression line was plotted covering 0 to 90% mortality range, and the $LC_{90}$ derived by eye from the graphs. The results are shown in the following table for preparations useful in the invention and the standard AMBUSH C cypermethrin emulsifiable concentrate and the standard DECIS deltamethrin emulsifiable concentrate.

| | $LC_{90}$ (ppm) |
|---|---|
| DECIS | >100.0 |
| AMBUSH | 301.0 |
| Preparation 1 | 25.0 |
| Preparation 3 | 131.0 |

The above table shows that microemulsion formulations of both deltamethrin and cypermethrin are greatly superior to the standard for the control of pyrethroid-resistant glasshouse whitefly at an $LC_{90}$ concentration.

EXAMPLE 8

Formulations useful in the present invention were tested against the adult black vine weevil. Ten weevils to be exposed to a spray of the formulation under test were placed under a Potter Tower, and then transferred to clean Petri dishes with untreated food. There were three replicate dishes per product. The application rate was 50 active ingredient per hectare. Mortality was assessed at from 12 to 24h after exposure, as appropriate, and after seven days. The following table shows the mean percentage mortality of the weevils for preparations useful in the invention, compared to a standard DECIS deltamethrin emulsifiable concentrate preparation and a standard AMBUSH cypermethrin emulsifiable concentrate preparation.

| FORMULATION | Assessment Time After Treatment | |
|---|---|---|
| | 24 HOURS | 7 DAYS |
| CONTROL (Water) | 0 | 1.7 ± 0.06 |
| Deltamethrin Treatments | | |
| DECIS | 0 | 33.3 ± 14 |
| Preparation 1 | 5 | 48.3 ± 15.9 |
| Cypermethrin Treatments | | |
| AMBUSH | 0 | 13.3 ± 13.3 |
| Preparation 3 | 0 | 73.3 ± 14 |

It can be seen that the formulation of Preparation 3 is significantly superior to the AMBUSH cypermethrin standard.

EXAMPLE 9

The formulation of Preparation 5 was tested against the house fly (Musca domestica) by measuring the total numbers of M. domestica knocked down during exposure to the formulation (deltamethrin applied at 8mg/m²) sprayed onto three surfaces. The results are shown in the following table, in which the abbreviation KD stands for knock down.

| Surface | Strain | Weeks after spraying | Total KD of 5 replicates at count times (h) | | | | | | | |
|---|---|---|---|---|---|---|---|---|---|---|
| | | | 1 | 2 | 3 | 4 | 5 | 6 | 24 | 48 |
| Plywood | Cooper | 0 | 100 | 100 | 100 | 100 | 100 | 100 | 100 | 100 |

-continued

| Surface | Strain | Weeks after spraying | Total KD of 5 replicates at count times (h) | | | | | | | |
|---|---|---|---|---|---|---|---|---|---|---|
| | | | 1 | 2 | 3 | 4 | 5 | 6 | 24 | 48 |
| | | 4 | 97 | 99 | 100 | 100 | 100 | 100 | 100 | 100 |
| | | 12 | 100 | 100 | 100 | 100 | 100 | 100 | 100 | 99 |
| | $R_1$ | 0 | 23 | 79 | 68 | 40 | 13 | 12 | 17 | 11 |
| | | 4 | 15 | 64 | 51 | 41 | 33 | 13 | 15 | 15 |
| | | 12 | 50 | 78 | 59 | 32 | 15 | 12 | 22 | 12 |
| | $R_2$ | 0 | 1 | 4 | 5 | 3 | 1 | 3 | 3 | 3 |
| | | 4 | 0 | 4 | 3 | 3 | 5 | 4 | 0 | 2 |
| | | 12 | 0 | 4 | 4 | 0 | 1 | 4 | 0 | 0 |
| Glass | Cooper | 0 | 100 | 100 | 100 | 100 | 100 | 100 | 100 | 100 |
| | | 4 | 100 | 100 | 100 | 100 | 100 | 100 | 100 | 100 |
| | | 12 | 100 | 100 | 100 | 100 | 100 | 100 | 100 | 100 |
| | $R_1$ | 0 | 100 | 100 | 100 | 100 | 100 | 100 | 99 | 99 |
| | | 4 | 100 | 100 | 100 | 100 | 100 | 99 | 96 | 97 |
| | | 12 | 100 | 100 | 100 | 99 | 100 | 99 | 94 | 98 |
| | $R_2$ | 0 | 89 | 93 | 85 | 83 | 71 | 52 | 56 | 65 |
| | | 4 | 99 | 100 | 100 | 98 | 97 | 95 | 73 | 90 |
| | | 12 | 99 | 98 | 96 | 92 | 89 | 79 | 64 | 59 |
| Vinyl tile | Cooper | 0 | 42 | 100 | 100 | 100 | 97 | 97 | 95 | 93 |
| | | 4 | 7 | 62 | 64 | 72 | 67 | 66 | 52 | 42 |
| | | 12 | 2 | 27 | 51 | 55 | 53 | 44 | 15 | 9 |
| | $R_1$ | 0 | 34 | 57 | 58 | 51 | 49 | 41 | 39 | 38 |
| | | 4 | 7 | 18 | 10 | 8 | 3 | 5 | 3 | 3 |
| | | 12 | 0 | 0 | 1 | 2 | 0 | 0 | 0 | 0 |
| | $R_2$ | 0 | 21* | 27* | 26* | 22* | 21* | 21* | 20 | 20* |
| | | 4 | 0 | 0 | 0 | 0 | 0 | 0 | 0 | 0 |
| | | 12 | 0 | 0 | 0 | 0 | 0 | 0 | 0 | 0 |

*Total KD occurred in 1 replicate (20).

The formulation of Preparation 5 performed best against the susceptible (Cooper) strain on glass with 100% knock down in all tests. The performance on plywood was almost as good, but on vinyl, total knock down was only obtained at the 2, 3 and 4h count periods. Good activity was also noted against the deltamethrin resistant ($R_1$ and $R_2$) strains.

I claim:

1. A method of treating wood or timber, the method comprising applying to the wood or timber a pesticidal water-miscible formulation whose average particle size is at most 200 nm.

2. A method as claimed in claim 1, wherein the method is a method of controlling at least one pest selected from the group consisting of the common furniture beetle (Anobium punctatum), the house longhorn (Hylotrupes bajulus) and the death watch beetle (Xestobium rufovillorum).

3. A method as claimed in claim 1, wherein the method is a method of controlling at least one of dry rot (Serpula (merulius) lacrymans) and wet rot (Coniophora puteena).

4. A method as claimed in claim 3, wherein the formulation comprises water, a pesticidal oil, a surfactant and a cosurfactant.

5. A method as claimed in claim 4, wherein the pesticidal oil consists substantially only of a pesticide.

6. A method as claimed in claim 4, wherein the cosurfactant has an HLB of less than 12.

7. A method as claimed in claim 1, wherein the surfactant comprises an anionic surfactant.

8. A method as claimed in claim 1, wherein the cosurfactant comprises a nonionic surfactant or an aliphatic alcohol.

9. A method as claimed in claim 1, wherein the formulation comprises on a w/v basis: oil (20 to 50%), surfactant (1 to 20%), cosurfactant (1 to 20%) and water (20 to 70%), provided that the total number of percentage parts of the ingredients cannot exceed 100.

10. A method as claimed in claim 1, wherein the formulation comprises on a w/v basis: oil (1 to 20%), surfactant (1 to 10%), cosurfactant (1 to 10%) and water (40 to 95%), provided that the total number of percentage parts of the ingredients cannot exceed 100.

11. A method as claimed in claim 4, wherein the cosurfactant comprises a nonionic surfactant.

12. A method as claimed in claim 4, wherein the cosurfactant is oil-soluble.

13. A method as claimed in claim 4, wherein the pesticide is a pyrethroid.

14. A method as claimed in claim 1, wherein the formulation is a microemulsion.

15. A method as claimed in claim 1, wherein the formulation is an oil-in-water microemulsion, a micellar solution or a molecular solution.

16. A method as claimed in claim 14, wherein the microemulsion is a water-in-oil microemulsion.

17. A method as claimed in claim 16, wherein the cosurfactant has an HLB of 4 to 9.

18. A method as claimed in claim 15, wherein the formulation is an oil-in-water microemulsion and the cosurfactant has an HLB of 9 to 20.

19. A method as claimed in claim 4, wherein the cosurfactant comprises an aliphatic alcohol.

* * * * *